United States Patent
Teufel et al.

(10) Patent No.: US 10,624,670 B2
(45) Date of Patent: Apr. 21, 2020

(54) SEALING DEVICE FOR SEALING A LEAD-THROUGH FOR A MEDICAL INSTRUMENT

(71) Applicant: KARL STORZ GmbH & Co. KG, Tuttlingen (DE)

(72) Inventors: Felix Teufel, Tuttlingen (DE); Annika Mueller, Geislingen (DE); Sebastian Wagner, Bretten (DE)

(73) Assignee: KARL STORZ SE & Co. KG, Tuttlingen (DE)

( * ) Notice: Subject to any disclaimer, the term of this patent is extended or adjusted under 35 U.S.C. 154(b) by 118 days.

(21) Appl. No.: 14/931,081

(22) Filed: Nov. 3, 2015

(65) Prior Publication Data
US 2016/0120573 A1  May 5, 2016

(30) Foreign Application Priority Data

Nov. 3, 2014 (DE) .................. 10 2014 115 985

(51) Int. Cl.
*A61B 17/34* (2006.01)
*F16J 15/02* (2006.01)

(52) U.S. Cl.
CPC ...... *A61B 17/3417* (2013.01); *A61B 17/3462* (2013.01); *A61B 17/3498* (2013.01); *F16J 15/022* (2013.01)

(58) Field of Classification Search
CPC ............ A61B 17/3417; A61B 17/3462; A61B 17/3498; A61M 2039/0626; A61M 2039/0673; A61M 1/282; A61M 1/28; A61M 1/284; A61M 2039/064

USPC ......... 604/247, 256, 167.01, 167.02, 167.03, 604/167.04, 244, 250
See application file for complete search history.

(56) References Cited

U.S. PATENT DOCUMENTS

| | | | |
|---|---|---|---|
| 4,430,081 A | 2/1984 | Timmermans | |
| 4,857,062 A | 8/1989 | Russell | |
| 5,300,033 A * | 4/1994 | Miller ............... | A61M 39/06 137/844 |
| 5,366,446 A | 11/1994 | Tal et al. | |

(Continued)

FOREIGN PATENT DOCUMENTS

| | | |
|---|---|---|
| DE | 29 30 514 A1 | 2/1981 |
| EP | 0 746 359 B1 | 9/2002 |

(Continued)

*Primary Examiner* — Kevin C Sirmons
*Assistant Examiner* — Tezita Z Watts
(74) *Attorney, Agent, or Firm* — Muncy, Geissler, Olds & Lowe, P.C.

(57) ABSTRACT

A sealing device for sealing a lead-through for a medical instrument that includes a fastening region for fastening the sealing device on a tube or other medical device, a ring-like supporting region which is connected to the fastening region, and an annular sealing lip with an outer edge which is connected to an inner edge of the support portion, and an inner edge which is provided and designed to fluid-tightly abut at an outer surface of a shaft inserted in the sealing device. The difference of the average diameter of the inner edge of the support portion and the mean diameter of a shaft of a medical instrument, for which the sealing device is provided and designed, is not larger than the difference of the average diameter of the shaft and the mean diameter of the inner edge of the sealing lip.

18 Claims, 5 Drawing Sheets

(56) References Cited

U.S. PATENT DOCUMENTS

| | | | | |
|---|---|---|---|---|
| 5,476,475 A | * | 12/1995 | Gadberry | A61B 17/3462 251/149.1 |
| 5,584,850 A | * | 12/1996 | Hart | A61B 17/3498 604/278 |
| 5,657,963 A | * | 8/1997 | Hinchliffe | A61M 39/06 251/149.1 |
| 5,752,938 A | * | 5/1998 | Flatland | A61B 17/3462 604/167.01 |
| 5,779,697 A | * | 7/1998 | Glowa | A61B 17/3462 606/185 |
| 6,123,689 A | | 9/2000 | To et al. | |
| 6,551,282 B1 | | 4/2003 | Exline et al. | |
| 6,811,546 B1 | | 11/2004 | Callas et al. | |
| 6,942,671 B1 | * | 9/2005 | Smith | A61B 17/3462 606/108 |
| 7,803,135 B2 | | 9/2010 | Franer | |
| 9,149,294 B2 | * | 10/2015 | Webb | A61M 39/0247 |
| 9,622,776 B2 | * | 4/2017 | Oberlaender | A61B 17/3462 |
| 2005/0165433 A1 | * | 7/2005 | Haberland | A61B 17/3462 606/167 |
| 2008/0065111 A1 | | 3/2008 | Blumenkranz et al. | |
| 2014/0222022 A1 | * | 8/2014 | Oberlaender | A61B 17/3462 606/130 |

FOREIGN PATENT DOCUMENTS

| | | |
|---|---|---|
| EP | 2 016 972 A2 | 1/2009 |
| WO | WO 91/12838 A1 | 9/1991 |
| WO | WO 93/01850 A1 | 2/1993 |
| WO | WO 98/32484 A1 | 7/1998 |
| WO | WO 99/42152 A1 | 8/1999 |
| WO | WO 2005/092217 A1 | 10/2005 |
| WO | WO 2007/121425 A1 | 10/2007 |
| WO | WO 2014/130636 A1 | 8/2014 |

* cited by examiner

SEALING DEVICE FOR SEALING A LEAD-THROUGH FOR A MEDICAL INSTRUMENT

This nonprovisional application claims priority under 35 U.S.C. § 119(a) to German Patent Application No. 10 2014 115 985.3, which was filed in Germany on Nov. 3, 2014, and which is herein incorporated by reference.

BACKGROUND OF THE INVENTION

Field of the Invention

The present invention relates to a sealing device for sealing a lead-through for a medical instrument, in particular for sealing the gap between a tube and a shaft of a medical instrument disposed in the tube during a micro-invasive procedure.

Description of the Background Art

An example of micro-invasive medical methods is laparoscopy. By means of a trocar, artificial access to the abdominal cavity of a patient is created through the abdominal wall. Through the lumen of a trocar tube remaining in the abdominal wall during laparoscopic surgery, an endoscope and/or other medical instruments (e.g. forceps, scissors, needle holders) may be introduced into the abdominal cavity. During laparoscopy, the abdomen is filled with carbon dioxide or another gas to create a pneumoperitoneum, a medical procedure-enabling cavity. Without special measures, this gas would escape through the tube. Therefore, numerous approaches were designed to occlude the lumen of the trocar tube as fluid-tight as possible, both when empty and when an instrument is inserted.

In part similar problems may arise in a working channel of an endoscope or when inserting a catheter into a blood vessel. In the latter case, however, not the escape of gas is to be prevented, but the escape of blood.

In U.S. Pat. No. 4,857,062, a valve for introducing a catheter into an artery is described. For sealing, a flexible element is provided, which is compressed to form a fluid-tight seal with a catheter.

In WO 93/01850 A1, a lever-operated seal for a tube is described. A wall made of an elastomer with an opening is stretched during insertion of an instrument into the tube through a plurality of levers, wherein the opening is increased.

In U.S. Pat. No. 5,366,446, an introducer assembly for use on the skin of a patient is described, which is designed for the insertion of tubes with different outside diameters. The assembly comprises a membrane made of a pierceable, elastomeric material in the center of a bellows.

EP 0 746 359 B1 describes a catheter check valve. For sealing, a rubber seal having an opening and a distal duckbill valve with a straight slot are provided.

In U.S. Pat. No. 4,430,081 a cannula is described for use with angiographic catheters. To seal against the entry of air or the leakage of blood from a blood vessel, a first seal having a slot, a second seal with a hole, and a third seal with a valve therein are provided, which are disposed adjacent to one another.

In WO 91/12838 A1, an infusion port is provided with several successively arranged resilient discs, each having circular openings or star-shaped slots which are arranged rotated against each other.

WO 98/32484 A1 describes a catheter introducer with a hemostasis valve. A sealing element comprises two perforated supporting discs, between which a sealing disc of soft-elastic foam plastic is provided with radially extending slots.

In U.S. Pat. No. 6,551,282 B1, a seal for sealing a tube when the shaft of an endoscope is inserted, is described. A wide annular seal is surrounded by a more rigid ring.

The sealing devices described each have specific advantages and disadvantages. A substantial and reliable sealing effect can be achieved easily with a sealing lip that presses with a very high contact pressure against the outer surface of the shaft of an instrument. However, this creates high sliding and static friction. A thin and/or soft sealing lip generates only very little sliding and static friction. However, it is not only less robust, it also has a reduced effect during lateral displacement of the shaft in the sealing device.

In all known thin and soft sealing lips, when you change the direction of movement of a shaft in the sealing device, a folding of the sealing lip is observed, which is accompanied by an appreciable change in the acting force between the shaft and the sealing device. This change in force can cause an involuntary movement of the shaft, or a movement that does not exactly correspond to the intentions of the medical staff, which can be bothersome or may even endanger the patient.

SUMMARY OF THE INVENTION

It is an object of the present invention to provide an improved sealing device, which in particular meets the listed requirements and expectations in balanced proportions.

Many conventional sealing devices have the widest possible sealing lips to offer low resistance to the movement of a shaft of an instrument in the sealing device, in a direction orthogonal to the longitudinal axis of the shaft, and to enable usability with shafts of different diameters. Further, the use of wider sealing lips was based on the assumption that due to their large elasticity, these offer only small resistance to an axial movement of a shaft, relative to the sealing device. The present invention is based on the realization that the broad sealing lips create more of a problem than that they offer a solution. Wide sealing lips must have a certain minimum wall thickness to not be puffed up or deformed, for example, by the overpressure in the pneumoperitoneum. Using these for many different shaft diameters then inevitably results in large mechanical stress with a large shaft diameter, which in turn increases the friction.

Incidentally, the mobility of a shaft relative to the sealing device in a direction orthogonal to the longitudinal axis of the shaft is not achievable only by using wide and elastic sealing lips. In the aforementioned U.S. Pat. No. 6,551,282 B1, it can be understood from FIGS. 4 and 5 that said mobility can also be ensured by other parts of the sealing device. The same is true for U.S. Pat. No. 7,803,135 B2. However, it is not apparent from the two documents, whether that knowledge was present. In any case, the authors of U.S. Pat. No. 6,551,282 B1 did not depart from the basic approach of broader sealing lips. The authors of U.S. Pat. No. 7,803,135 B2 noticeably embarked on a path that deviates from the approach described below.

Embodiments of the present invention are based on the idea of allowing a displacement of a shaft in a sealing device in a direction orthogonal to the longitudinal axis of the shaft not by means of the sealing lip, but by designing the sealing lip comparatively narrow. Said displacement must then be provided by other means, but the sealing lip can be designed relatively thin without the risk of deformation by a difference in pressure. A support region surrounding the sealing lip with comparatively low elasticity on the one hand, and a precise adjustment of the sealing lip to a predetermined shaft diameter, can achieve a reliable sealing effect and at the same time low friction and little force variation in the folding of the sealing lip upon a change in direction.

Further, embodiments of the present invention are based on the recognition that the folding of the sealing lip upon changing the direction of movement of a shaft in the sealing device is particularly noticeable and distracting when it occurs simultaneously along the entire circumference of the sealing lip, and that this is aided by the conventional rotation-symmetrical embodiment of sealing devices and their sealing lips. Embodiments of the present invention are therefore based on the idea of breaking the rotational symmetry of the sealing lip in order to promote a, not simultaneous but gradual, folding of the sealing lip—starting from one point and spreading along its periphery.

A sealing device for sealing a lead-through for a shaft of a medical instrument includes a fastening area for fastening the sealing device on a tube or other medical device, a ring-like support portion which is connected to the fastening portion, and an annular sealing lip having an outer edge which is connected to an inner edge of the support portion, and an inner edge that is provided and designed to fluid-tightly abut an outer surface of a shaft inserted into the sealing device, whereas the difference $U_2-U_S$ of the circumference $U_2$ of the inner edge of the support portion and the circumference $U_S$ of a shaft of a medical instrument for which the sealing device is provided and formed is not greater than the difference $U_S-U_1$ of the circumference $U_S$ of the shaft and the circumference $U_1$ of the inner edge of the sealing lip in its stress-free state ($U_2-U_S \leq U_S-U_1$), or the difference $D_2-D_S$ of the mean diameter $D_2$ of the inner edge of the support portion and the average diameter $D_S$ of a shaft of a medical instrument, for which the sealing device is provided and designed, is not greater than the difference $D_S-D_1$ of the average diameter $D_S$ of the shaft and of the mean diameter $D_1$ of the inner edge of the sealing lip $D_2-D_S \leq D_S-D_1$.

The condition mentioned for the circumferences may alternatively be formulated such that the arithmetic mean value $(U_1+U_2)/2$ of the circumference $U_1$ of the inner edge of the sealing lip and the circumference $U_2$ of the inner edge of the support portion is not greater than the circumference $U_S$ of a shaft of a medical instrument, for which the sealing device is provided and designed ($(U_1+U_2)/2 \leq U_S$). The condition mentioned for the average diameter can alternatively be formulated such that the arithmetic mean $(D_1+D_2)/2$ of the average diameter $D_1$ of the inner edge of the sealing lip and the mean diameter $D_2$ of the inner edge of the support portion is no greater than the mean diameter $D_S$ of a shaft of a medical instrument, for which the sealing device is provided and designed.

A sealing device for sealing a lead-through for a shaft of a medical instrument includes a fastening area for fastening the sealing device on a tube or other medical device, a ring-like support portion, which is connected to the fastening area, and an annular sealing lip having an outer edge which is connected to an inner edge of the support portion, and an inner edge which is provided and designed to fluid-tightly abut an outer surface of a shaft inserted into the sealing device, wherein the periphery of the inner edge of the sealing lip is at least six tenths and a maximum of nine tenths of the periphery of a shaft of a medical instrument, for which the sealing device is provided and designed.

A sealing device for sealing a lead-through for a shaft of a medical instrument comprises a fastening region for fastening the sealing device on a tube or other medical device, a ring-like support portion which is connected to the fastening portion, and an annular sealing lip having an outer edge which is connected to an inner edge of the support portion, and an inner edge, which is provided and designed to fluid-tightly abut an outer surface of a shaft inserted into the sealing device, wherein in particular the average thickness of the sealing lip is at most a fifth of the average thickness of the support portion.

The sealing lip of the sealing device described herein is in each case in particular membrane-like. In particular, the sealing lip has a constant thickness or a thickness varying in each case only slightly in the radial direction and/or in the circumferential direction (in particular, by a factor of two or less).

In so far as the inner edges of the support portion and the sealing lip, and the outer contour of the cross section of the shaft of a medical instrument, for which the sealing device is provided and designed, are each circular, the average diameters, the diameters, and the conditions for the circumferences and diameters are equivalent. The diameter of the circle is considered the average diameter of an edge, which differs only in sections, which together account for less than half or less than one third of the circumference of the edge, from the shape of a circle. The diameter of a circle with an area that corresponds to the content of the surface defined by the edge is viewed as the average diameter of another non-circular periphery.

When the support portion and the sealing lip comprise the same material and are formed in one piece, and no step-shaped change in thickness between the support portion and the sealing lip is present, the inner edge of the support portion is the (linear) number of locations at which the force that sets the sealing device against a deformation through a shaft of a medical instrument, for which the sealing device is provided and designed, greatly increases. The inner edge of the support portion is, for example, the (linear) number of locations at which the force that sets the sealing device against a deformation through a shaft of a medical instrument, to which the sealing device is provided and designed, is doubled or tripled, or fivefold or tenfold, as compared with the minimum value. The inner edge of the support portion is in particular the line at which the thickness of the sealing device is equal to the arithmetic average of the minimum thickness of the sealing lip and the maximum thickness of the support portion, or 90% of the thickness of the support portion. When the support portion has the shape of a ring-like section of a plate with a constant thickness and merges continuously into the sealing lip, then the inner edge of the support portion, in particular the inner edge of the plate-shaped area, is of constant thickness. The outer edge of the support portion is, for example, situated where the supporting portion merges into a substantially cylindrical wall or directly into a fastening region.

The sealing device is particularly suitable for sealing the annular or ring-like space between the inner surface of a tube of a trocar and the outer surface of a shaft of a medical instrument arranged in a tube. The medical instrument, for example, is an endoscope or other medical instrument for use in micro-invasive medical procedures. The sealing device is provided and designed for a medical instrument having a shaft with a predetermined cross-section, in particular with a circular cross-section with a predetermined diameter. In order to avoid confusion or accidental use of a shaft cross-section for which the sealing device is not provided and designed, the sealing device can be clearly identified with an alphanumeric label, a symbol or color. In particular, the shaft diameter for which the sealing device is provided and designed, can be indicated alphanumerically on the sealing device.

The support portion and the sealing lip may be made of the same material. In particular, the entire sealing device is formed in one piece, for example as a cast part, that includes the fastening region, the support region and the sealing lip. Alternatively, the sealing lip on the one hand, and the support region and/or fastening region can be made of different materials, wherein regions having different materials are connected with one another, in particular integrally or positively. For example, the sealing lip may be designed of a comparatively soft material, and the support region or a portion of the support region or the cylindrical wall 38 may be made of a relatively hard material.

The fastening portion comprises, for example, an inwardly projecting collar at the distal edge, i.e. the edge that is to face the patient and the tube, which can form a positive mechanical connection with a groove at the proximal edge, or the edge of a tube or other medical device that is to face the sealing device.

The sealing device is in particular partially or completely made of a silicone elastomer, another elastomer or other elastic material. The material of the sealing device or at least the material of the sealing lip in particular has a hardness of about 40 Shore A. The elasticity of the material, in particular in the fastening region, can allow for the formation and the dissolution of a positive mechanical connection of the sealing device with a tube or other medical device.

A support region or a sealing lip is ring-like if the supporting portion or the sealing lip has the topology of a circular ring, i.e. is doubly connected in the mathematical sense. Neither the annular support area nor the annular sealing lip must form a circular ring. The inner and outer edges of the support portion and the sealing lip can each be circular, elliptical, oval, polygonal, or have another shape.

A sealing device with the described features can have a very narrow sealing lip, that is, a sealing lip, in which the difference of the diameters or the difference of the circumferences of the outer and the inner edge is small, without causing a cancellation of the sealing action with a lateral displacement of a shaft inserted into the sealing device. A narrow sealing lip may in turn be formed with particularly thin walls, and particularly elastically, without impairing the sealing action. A thin-walled and elastic design of the sealing lip can reduce the friction between the sealing lip and a shaft and can minimize the effect of the folding of the sealing lip upon reversal of the direction of movement of a shaft in the sealing direction.

In a sealing device, as described herein, the sealing lip in particular is not rotationally symmetrical to the longitudinal axis of a shaft inserted in the sealing device in the designated center position and orientation.

A sealing device for sealing a lead-through for a shaft of a medical instrument includes a fastening area for fastening the sealing device on a tube or other medical device and an annular sealing lip with an inner edge which is provided and designed to fluid-tightly abut an outer surface of a shaft inserted into the sealing device, wherein the sealing lip is not rotationally symmetrical to the longitudinal axis of a shaft inserted in the sealing device in the designated center position and orientation.

In the case of a shaft with a straight, circular cylindrical surface, the longitudinal axis of the shaft is the axis of symmetry of this surface. The designated center position and orientation of a shaft in the sealing device results from the geometry of the sealing device. For example, the distal edge and/or the fastening device near the distal edge of the sealing device is rotationally symmetrical to the longitudinal axis of a shaft inserted in the designated orientation and central position in the sealing device. Further, the position and the orientation of the longitudinal axis of the shaft inserted in the sealing device in the designated center position and orientation are usually predetermined by the tube or the medical device (in particular by their axis of symmetry) for which the sealing device is provided and designed.

In addition to the fact that the sealing lip is not rotationally symmetrical to the longitudinal axis of a shaft inserted in the designated center position and orientation in the sealing device, the sealing lip cannot be rotationally symmetrical to the longitudinal axis of a shaft inserted into the sealing device when the mechanical stress state of the sealing device is the lowest.

A non-rotationally symmetrical design of the sealing lip may have the consequence that forces and mechanical stresses present in the sealing lip, and forces acting along the inner edge of the sealing lip between the sealing lip (in particular its inner edge) and an outer surface of a shaft, may vary. During a reversal of the direction in which a shaft is moved in the sealing device this can cause a gradual folding of the sealing lip emanating from one place on the inner edge of the sealing lip and slowly extending therefrom. The effect of the folding, which is called snapping by users of conventional sealing devices, can thus be significantly reduced. This may enable a more sensitive moving of a shaft of a medical instrument in the sealing device and may reduce the risk of an involuntary movement of the shaft, or a movement that does not exactly correspond to the intentions of the medical staff, which can be bothersome or can even endanger the patient.

A sealing device as described herein in particular further comprises a ring-like support portion which is connected to the fastening region, wherein an outer edge of the sealing lip is connected to the inner edge of the support portion.

In a sealing device, as described herein, in particular at least either the inner edge or the outer edge of the sealing lip is not circular.

In the case of a sealing device, as described herein, in particular the centroid of the surface bounded by the inner edge of the sealing lip is spaced from the centroid of the surface bounded by the outer edge of the sealing lip.

In the case of a sealing device, as described herein, the sealing lip has a thickness varying in the direction of its circumference, especially in a mechanically stress-free state.

In a sealing device, as described herein, in particular the surface normals of two surfaces of the sealing lip averted from each other, located opposite each other on the surfaces in a mechanically stress-free state of the sealing lip, are not parallel.

The surface normals of two surfaces of the sealing lip facing away from each other at opposite locations on the surfaces form, in particular, an angle in the range of 1 degree to 3 degrees or in the range of 1.5 degrees to 2 degrees. The described non-parallelism of the surface normal exists in particular for the entire surface of the sealing lip or for at least half of the area of the sealing lip.

In a sealing device, as described herein, the inner edge of the sealing lip has in particular the shape of a section of a lateral surface of a cylinder, of which the symmetry axis is not parallel to the average surface normal of two surfaces of the sealing lip facing away from one another.

The inner edge of the sealing lip in particular has the shape of a section of a lateral surface of an oblique circular cylinder or other cylinder. The symmetry axis, i.e. the direction of the translation invariance of the lateral surface of the cylinder, forms with the middle surface normal of two surfaces facing away from one another in particular an angle of at least 5 degrees or at least 10 degrees or at least 20 degrees or at least 30 degrees. The average surface normal is in particular the average value or half the difference of the normalized integral of the surface normals over the two surfaces of the sealing lip facing away from each other.

In a sealing device, as described herein, the inner edge of the sealing lip is in particular rounded, for example with a circular arc-shaped cross section.

In a sealing device, as described herein, the sealing lip in particular has a thickness continuously increasing outwardly from the inner edge of the sealing lip.

In a sealing device, as described herein, the average surface normal of the sealing lip is in particular not parallel to the longitudinal axis of a shaft inserted in the designated center position and orientation in the sealing device.

The average surface normal of the sealing lip is in particular the normalized integral of the surface normal of one of two surfaces of the sealing lip facing away from each other over the entire sealing lip. Alternatively, the average surface normal is, for example, the average or half the difference of the normalized integral of the surface normals over the two surfaces of the sealing lip facing away from each other. The angle between the average surface normal and the longitudinal axis of a shaft inserted in the designated center position and orientation in the sealing device is in particular at least 5 degrees or at least 10 degrees or at least 20 degrees or at least 30 degrees.

In a sealing device, as described herein, the support region is in particular parallel or substantially parallel to a plane that is not parallel to the longitudinal axis of a shaft inserted in the designated center position and orientation in the sealing device.

The entire support portion or a proximal surface area and/or a distal surface portion of the support portion may each have substantially the shape of a—in particular annular—section of a plane of which the normal is not parallel to the longitudinal axis of a shaft inserted in the designated center position and orientation in the sealing device.

Further, the entire supporting area or a proximal surface area and/or a distal surface portion of the supporting portion may in each case form the—in particular annular—section of a curved surface such as a spherical surface or a surface of another spheroid.

Each of the described types (and types combined with each other) of a non-rotationally symmetrical design of the sealing lip may cause a variation of the forces between the sealing lip and the surface of an inserted shaft and/or the mechanical tension within the sealing lip, which may result in a gradual instead of a simultaneous folding of the sealing lip upon a change in direction of the movement of a shaft in the sealing device. The sealing lip is always provided and designed to—unlike a seal with one or more radial sections—abut along a circumferential line at the outer surface of an inserted shaft, thus developing full or substantial sealing action.

In a sealing device, as described herein, the perimeter of the inner edge of the sealing lip is at least six tenths and a maximum of nine tenths of the periphery of a shaft of a medical instrument, for which the sealing device is provided and designed.

In a sealing device, as described herein, the inner edge of the sealing lip is in particular substantially circular, and the diameter of the inner edge of the sealing lip is at least six tenths and a maximum of nine tenths of the diameter of a circular-cylindrical shaft of a medical instrument, for which the sealing device is provided and designed.

The circumference or the diameter of the inner edge of the sealing lip can alternatively amount to at least seven tenths and/or at most eight tenths of the circumference or diameter of a shaft, for which the sealing device is provided and designed.

When the shape of the inner edge of the sealing lip only deviates from an ideal circular shape in some sections, the diameter of the inner edge of the sealing lip in particular is meant to be the diameter of the circle.

A ratio of the circumferences or diameters of the inner edge of the sealing lip and the outer contour of the cross section of a shaft, for which the sealing device is provided and designed, in the range of six or seven-tenths up to eight or nine-tenths, can be achieved by a particularly favorable compromise between a good and reliable sealing effect on the one hand, and low friction between the shaft and the sealing device on the other.

In the case of a sealing device, as described herein, the mean thickness of the sealing lip is in particular at most a fifth of the average thickness of the support portion.

The thickness of the sealing lip is in particular approximately 0.3 mm. A ratio of the thickness of the sealing lip to the thickness of the support portion of not more than 1:5 creates on the one hand an elastic sealing lip and low friction between the sealing lip and the inserted shaft, and on the other a sufficiently rigid or stiff or non-resilient support portion to ensure a full or substantial sealing effect, even then when a shaft arranged in the sealing device is displaced in a direction orthogonal to its longitudinal axis relative to the sealing device. Sufficient rigidity of the support portion in this case means that the whole ring-like support region is displaced as soon as the shaft has completely deformed the sealing lip on one side and rests on the support region. The resulting, complete displacement of the support portion can ensure that the sealing lip rests completely on the shaft on the opposite side as well, and that it can fulfill its sealing function completely. This is especially true if at the same time the described conditions apply for the differences between the circumferences or diameters or for the arithmetic mean of the circumferences or diameters.

In a sealing device, as described herein, a displacement of the support portion relative to the fastening area can be possible, for example, due to an elasticity of a tubular wall of the sealing device which connects the support portion to the fastening portion. Alternatively, the sealing device for connection to a tube or other medical device that allows a displacement of the entire sealing device, may be provided and designed.

In a sealing device, as described herein, in particular one of two surfaces of the sealing lip facing away from each other is flush with one of two surfaces of the supporting portion facing away from each other.

In particular, the proximal surfaces, i.e. the surfaces of the sealing lip and the supporting area facing away from a tube or other medical device with which the sealing device is to be connected, are flush. For example, both proximal surfaces can be situated in a plane or on a spherical surface or a surface of another ellipsoid. Alternatively, the distal surfaces, i.e. the surfaces of the sealing lip and supporting region facing a tube or other medical device with which the sealing device is to be connected, can lie in a plane, on a spherical surface, or on a surface of another spheroid, or be flush in other ways.

The flush embodiment of surfaces of the sealing lip and the supporting portion can simplify its manufacturing, in particular the shape of the cast part to be used. A conical or other funnel-shaped embodiment of a transition region between the proximal surfaces of the supporting portion and the sealing lip can facilitate insertion of a shaft of a medical instrument in the sealing device.

In a sealing device, as described herein, the sealing lip in the mechanically tension-free state particularly has the shape of a cut-out of a plane, of a surface of a circular cone or an elliptic cone, of a surface of a pyramid, of a surface of a paraboloid of revolution or of another paraboloid, or of a surface of a sphere or other ellipsoid of revolution or other ellipsoid.

The sealing lip then especially finds itself in a mechanically unstressed condition, when no shaft of a medical instrument is inserted into the sealing device. The shape of the sealing lip in the mechanical stress-free state is in particular the shape of the sealing lip after manufacture of the sealing device and prior to its use. The sealing lip has in particular the shape of a ring-like or biconnected section of a plane or of a surface of a circular cone, an elliptic cone, a pyramid, a paraboloid or an ellipsoid. Provided that the sealing lip has the shape of a portion of a pyramid surface, the base of the pyramid has a particularly smooth (differentiable in the mathematical sense) or polygonal edge.

In a sealing device, as described herein, in particular at least a portion of the surface of the sealing lip has a friction-reducing coating or design.

A friction-reducing coating of the sealing device in particular comprises poly (p-xylylene), which is also marketed under the trade name Parylene.

A friction-reducing coating or design of the sealing lip can reduce the required forces to move a medical instrument in the sealing device in order to overcome the static friction and/or sliding friction, and can moreover prevent a folding of the sealing lips upon reversal in the direction of movement. Further, a friction-reducing coating or design of the surface can aid a gradual folding of the sealing lip with a change in the direction of movement of a shaft in the sealing device. Friction diminished by the coating may further diminish the risk of damage or destruction of the sealing device, for example, when inserting a pointed or sharp medical instrument.

A tube has a sealing device as described herein.

The tube is, in particular, the tube of a trocar.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

DETAILED DESCRIPTION

Figure 1:
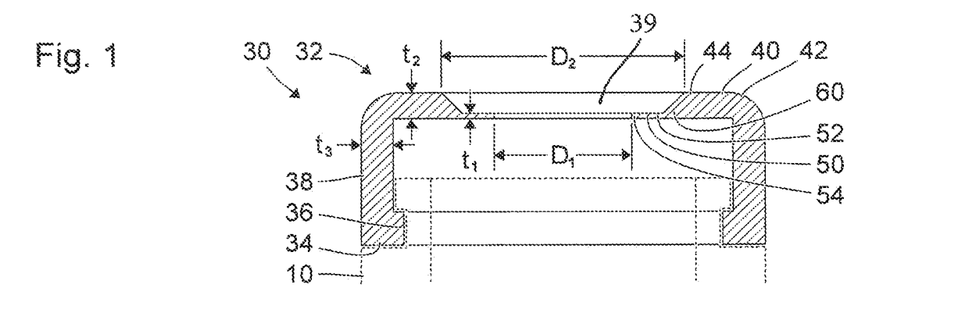
FIG. 1 is a schematic representation of a cross-section of a sealing device.

FIG. 1 shows a schematic representation of a cross-section of a sealing device 30 for sealing a lead-through 39 for a shaft of a medical instrument. The section plane of FIG. 1 includes an axis of symmetry, to which the sealing device 30 is rotationally symmetric.

The sealing device 30 is formed for the mechanical connection with a tube 10 of a trocar or other medical device. The tube 10 is not a part of the sealing device 30 and therefore indicated in FIG. 1 only transparently and with dashed contours. The sealing device 30 has a proximal side 32, i.e. a side 32 facing away from the trocar 10, and from the patient when in use, and a distal edge 24, i.e. an edge 34 facing the trocar 10. At or near the distal edge 34, an inwardly projecting collar 36 is provided for engagement in a corresponding groove on the trocar 10. Thus, the inwardly projecting collar 36 forms a fastening area of the sealing device 30. A cylindrical wall 38 connects the distal edge 34 with the inwardly projecting collar 36 on the one hand, and with the proximal side 32 of the sealing device 30 on the other.

The proximal side 32 of the sealing device 30 is formed by a ring-like support portion 40 and a sealing lip 50. The support portion 40 and the sealing lip 50 each have the shape of a circular ring-shaped cut-out on a plate. The outer edge 42 of the support portion 40 merges into the cylindrical wall 38 of the sealing device 30. The inner edge 44 of the support portion 40 is connected through a transition area 60 with the outer edge 52 of the sealing lip 50. The inner edge 54 of the sealing lip 50 is designated to abut against a shaft of a medical instrument to be inserted into the sealing device 30.

In the illustrated example, the distal surfaces, i.e. the surfaces facing the tube 10 and respectively oriented downward in FIG. 1, of the support portion 40 and the sealing lip 50 are flush and in particular in a plane. The proximal surfaces, i.e. the surfaces facing away from the tube 10 and upwardly oriented in FIG. 1, of the support portion 40 and the sealing lip 50 are in two planes spaced apart from each other. Therefore, the transition region 60 has a conical, proximal surface.

The sealing device 30 is in particular integrally formed and at the same time designed as a cast part with all the characteristics described. The sealing device 30 has for example a silicone elastomer or another elastomer or other resilient material. The material of the sealing device 30 in particular has a hardness of about 40 Shore A. In the aforementioned rotational symmetry of the sealing device 30, the outer edge 42 and inner edge 44 of the support portion 40, and the outer edge 52 and inner edge 54 of the sealing lip 50, are both circular, wherein all centers lie on the axis of symmetry of the sealing device 30.

The inner edge 54 of the sealing lip 50 has a diameter $D_1$. The inner edge 44 of the support portion 40 has a diameter $D_2$. The sealing device 30 is adapted and designed for use with the shaft of a medical instrument which has a diameter of $D_S$. The diameters $D_1$ and $D_2$ of the inner edges 54, 44 of the sealing lip 50 and the support portion 40 are selected such that $D_2-D_S \leq D_S-D_1$. In other words, the arithmetic mean $(D_1+D_2)/2$ is not larger than the average diameter $D_S$ of a shaft of a medical instrument, for which the sealing device 30 is provided and designed. A similar condition (equivalent for the circular edges 54, 44 and the cross-section) is $U_2-U_S \leq U_S-U_1$, wherein $U_1$ is the circumference of the inner edge 54 of the sealing lip 50, $U_2$ is the circumference of the inner edge 44 of the support portion 40, and $U_S$ is the circumference of a shaft of a medical instrument, for which the sealing device is provided and designed. This condition is mathematically identical with the condition that the arithmetic mean value $(U_1+U_2)/2$ of the circumference $U_1$ of the inner edge 54 of the sealing lip 50, and of the circumference $U_2$ of the inner edge 44 of the support portion 40 is not larger than the circumference $U_S$ of the shaft, $(U_1+U_2)/2 \leq U_S$.

Figure 2:
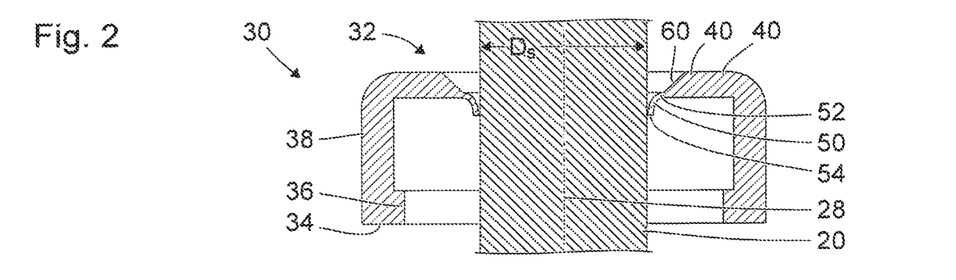
FIG. 2 is a further schematic representation of a cross-section of the sealing device from FIG. 1.
Figure 3:
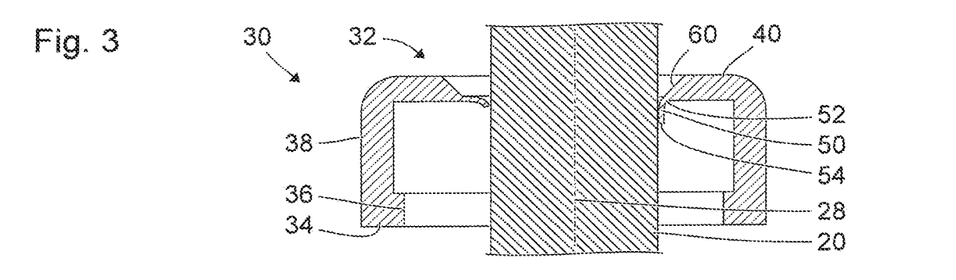
FIG. 3 is a further schematic representation of a cross-section of the sealing device from FIGS. 1 and 2.
Figure 4:
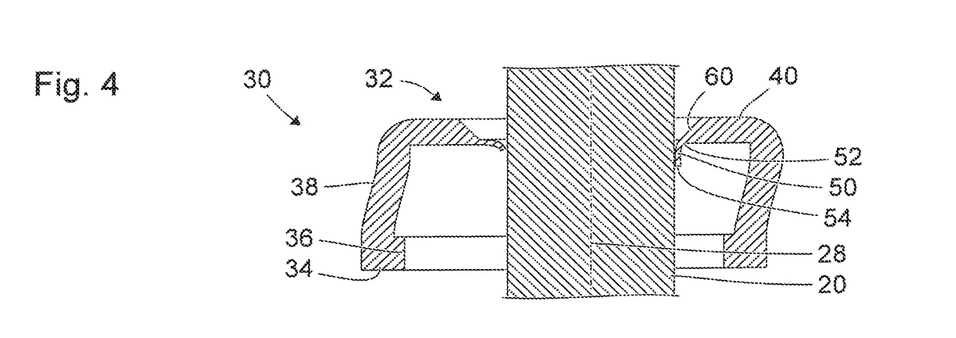
FIG. 4 is a further schematic representation of a cross-section of the sealing device of FIGS. 1 to 3.

The above-mentioned relationships between the diameters or circumferences ensure, as shown with reference to FIGS. 2 to 4, a complete sealing effect at any time.

The diameter $D_1$ of the inner edge 54 of the sealing lip 50 is between 60% and 90% of the diameter $D_S$ of a shaft of a medical instrument, to which the sealing device is provided and designed, $0.6\ D_S \leq D_1 \leq 0.9\ D_S$. This also contributes to the sealing action.

The sealing lip 50 has a thickness $t_1$. The support portion 40 has a thickness $t_2$. The cylindrical wall 38 has a thickness $t_3$. The thickness $t_1$ of the sealing lip 50 does not exceed one fifth of the thickness $t_2$ of the support region 40, $t_1/t_2 \leq 1/5$. This thickness ratio ensures that the sealing lip 50 has a much greater elasticity than the support area 40. As illustrated by FIGS. 2 to 4, this also contributes to the fact that the sealing effect of the sealing device 30 is preserved even under adverse conditions. For example, the thickness $t_1$ of the sealing lip 50 is about 0.3 mm and the thickness $t_2$ of the support portion 40 about 1.5 mm.

FIG. 2 shows a further schematic cross-sectional view of the sealing device 30 of FIG. 1. The type of display, in particular the sectional plane shown, corresponds to that of FIG. 1. In contrast to FIG. 1, the sealing device 30 is shown without a tube. In contrast to FIG. 1, a shaft 20 of a medical instrument in the sealing device 30 is shown in FIG. 2. The shaft 20 has a longitudinal axis 28, which in the situation shown coincides with the axis of symmetry of the sealing device 30 and is located in the sectional plane that is shown.

The inner edge 54 of the sealing lip 50 abuts the outer surface of the shaft 20 in an area which annularly surrounds the shaft 20. This way, the sealing lip 50 unfolds the designated sealing effect. Since the diameter $D_S$ of the shaft 20 is larger than the diameter $D_1$ of the inner edge 54 of the sealing lip 50 in its mechanically stress-free state (see FIG. 1), the sealing lip 50 is deformed. The resulting mechanical tension within the sealing lip 50 causes a contact pressure of the sealing lip 50, in particular of its inner edge 54, on the outer surface of the shaft 20. This contact pressure promotes the sealing effect. However, it also creates sliding and static friction between the sealing lip 50 and the shaft 20. Due to the small thickness $t_1$ of the sealing lip 50, the contact pressure of the sealing lip 50 on the outer surface of the shaft 20, and the friction between these, is relatively small.

The deformation of the sealing lip 50 illustrated in FIG. 2 results in particular during insertion of the shaft 20 from proximal to distal, or in FIG. 2, from top to bottom. After a reversal of the direction of movement of the shaft 20 relative to the sealing device 30 and a movement of the shaft 20 relative to the sealing device 30 in the proximal direction, the sealing lip 50 can be folded over, after which the inner edge 54 of the sealing lip 50 is no longer oriented distally, but proximally. This folding is perceived by the medical staff as snapping and can cause an involuntary movement of the shaft 20, or a movement not exactly corresponding to the intentions of the medical staff. This may pose a risk of injury to a patient. Due to the low thickness of the sealing lip 50, the forces occurring during folding of the sealing lip 50 are relatively small.

FIG. 3 shows a further schematic representation of a section through the sealing device 30 of FIGS. 1 and 2. The type of display, in particular the section plane, corresponds to that of FIG. 1 and particularly to that of FIG. 2.

In contrast to FIG. 2, FIG. 3 shows a situation in which the shaft 20 is displaced relative to the sealing device 30 in a direction orthogonal to the longitudinal axis 28 of the shaft 20 and to the axis of symmetry of the sealing device 30. The shaft 20 is moved as far as possible with a maximum of exclusive deformation of the sealing lip 50 and without significant deformation of the support portion 40. Due to the described relationship between the diameters $D_1$, $D_2$ and $D_S$ of the inner edges 54, 44 of the sealing lip 50 and the support portion 40, as well as the shaft 20, the sealing lip 50 also abuts on the outer surface of the shaft 20 with the side opposite the maximum deformation, shown on the left in FIG. 3. This way, a complete sealing effect is still ensured.

FIG. 4 shows a further schematic representation of a section through the sealing device 30 of FIGS. 1 to 3. The type of representation, particularly the section plane, corresponds to that of FIG. 1, and in particular of FIGS. 2 and 3.

In FIG. 4, a situation is shown in which the shaft 20 is further displaced in the direction orthogonal to the longitudinal axis 28 of the shaft 20 relative to the sealing device 30 than in the situation shown in FIG. 3. In the example shown in FIG. 4, the cylindrical wall 38 is deformed. Alternatively, or additionally, the tube 10 indicated in FIG. 1 and not shown in FIG. 4 could be deformed. The large thickness $t_2$ of the support region 40 and its resulting low, mechanical elasticity causes the support portion 40 to not only be displaced at the same or at almost the same rate at the location of maximum deformation of the sealing lip 50 (in FIG. 4: right), but also on the opposite side (in FIG. 4: left). Therefore, the sealing lip 50 not only abuts the location of maximum deformation, but also completely abuts the opposite side at the outer surface of the shaft 20, where it develops its full sealing effect.

The sealing effect of the sealing device 30 shown with reference to FIGS. 2 to 4 with a significant displacement of the shaft 20 is present in particular if $t_1/t_2 \leq 1/5$ is true, because then the sealing lip 50 is sufficiently elastic and the support portion 40 is sufficiently inelastic.

Figure 5:
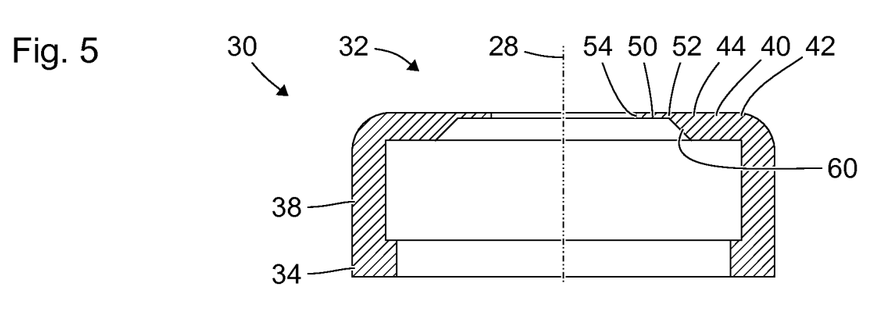
FIG. 5 is a schematic representation of a cross-section of a further sealing device.

FIG. 5 shows a schematic representation of a section through a further sealing device 30, which is similar in some features, properties and functions to the sealing device illustrated with reference to FIGS. 1 to 4. The type of display, in particular the section plane, corresponds to that of FIGS. 2 to 4 and especially of FIG. 1, wherein neither a tube nor a shaft of a medical instrument are indicated. Hereinafter, in particular features and characteristics are described in which the sealing device 30 shown in FIG. 5 differs from the sealing devices shown with reference to FIGS. 1 to 4.

In the sealing device shown in FIG. 5, the sealing lip 50 is arranged further proximally (in the Figures: further above), relative to the support portion 40. In particular, the proximal surface of the sealing lip 50 is arranged flush with the proximal surface of the support portion 40. The proximal surfaces of the sealing lip 50, the support portion 40 and the transition region 60 thus lie in one plane. The transition region 60 has a conical distal surface.

Figure 6:
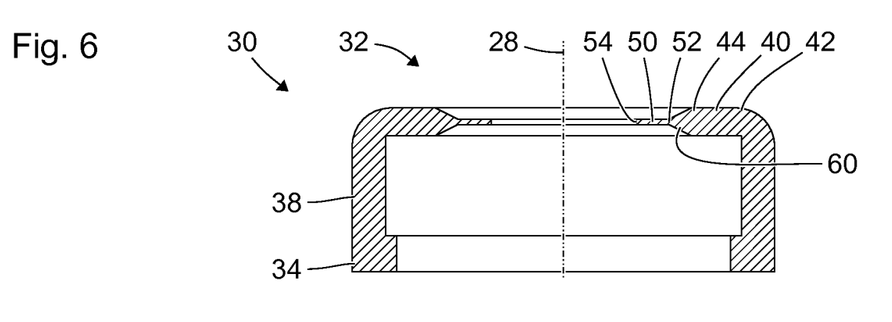
FIG. 6 is a schematic representation of a cross-section of a further sealing device.

FIG. 6 shows a schematic representation of a section through a further sealing device 30, which in some features, properties and functions is similar to the sealing device illustrated with reference to FIGS. 1 to 5. The type of display is similar to that of FIGS. 1 to 4 and particularly to that of FIG. 5. Below, in particular features, properties and functions are shown in which the sealing device shown in FIG. 6 differs from the sealing devices shown with reference to FIGS. 1 to 5.

In the sealing device shown in FIG. 6, the sealing lip 50 is disposed relative to the support portion 40 so that neither the proximal surfaces nor the distal surfaces of the sealing lip 50 and the support portion 40 are flush or lie in one plane. Instead, the transition region 60 has both proximally and distally tapered surfaces.

Figure 7:
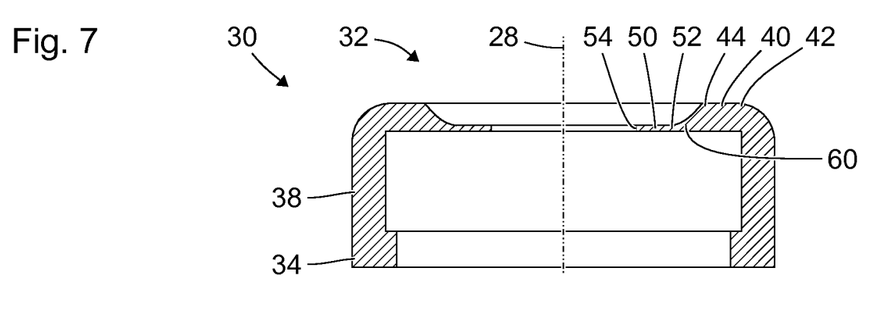
FIG. 7 is a schematic representation of a cross-section of a further sealing device.

FIG. 7 shows a schematic representation of a section through a further sealing device 30, which is similar in some features, properties and functions to the sealing device illustrated with reference to FIGS. 1 to 6. The type of display is similar to that of FIGS. 1 to 4 and particularly of FIGS. 5 and 6. Below, in particular the features, properties and functions are shown in which the sealing device shown in FIG. 7 differs from the sealing devices illustrated with reference to FIGS. 1 to 6.

In particular, the sealing device shown in FIG. 7 differs from the sealing device shown in FIG. 1 in particular in that the proximal surface of the transition area 60 between the sealing lip 50 and the support portion 40 is not tapered, but is formed generally more funnel-shaped, but with a rounded transition to the outer edge 52 of the sealing lip 50. The inner edge 44 of the support portion 40 is defined by a sharp edge towards the transition area 60. Alternatively, or additionally, a smooth transition to the transition area 60 may be provided at the inner edge 44 of the support portion 40. Accordingly, the tapered distal surfaces of the transition area 60 may also be rounded in the embodiments illustrated with reference to FIGS. 5 and 6.

Figure 8:
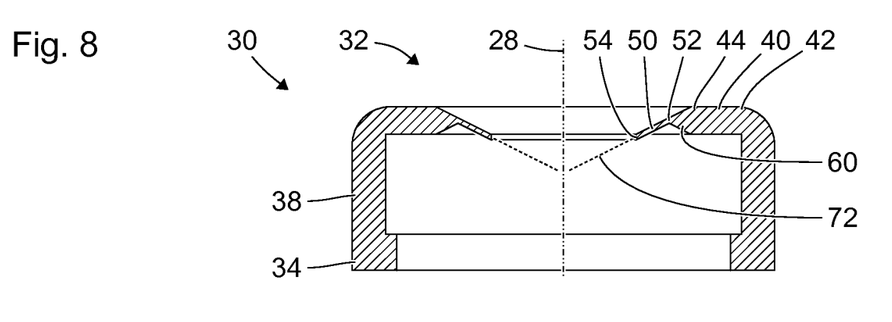
FIG. 8 is a schematic representation of a cross-section of a further sealing device.

FIG. 8 shows a schematic representation of a section through a further sealing device 30, which in some features, properties and functions is similar to the sealing devices shown with reference to FIGS. 1 to 7. The type of display corresponds to that of FIGS. 1 to 4 and particularly of FIGS. 5 to 7. Below, in particular, features, properties and functions are shown in which the sealing device shown in FIG. 8 differs from the sealing devices illustrated with reference to FIGS. 1 to 7.

The sealing device 30 illustrated in FIG. 8 differs from the sealing devices illustrated with reference to FIGS. 1 to 7 in particular in that the sealing lip 50 has the shape of an annular section of a cone or a circular cone 72, which is indicated in FIG. 8 with dashed lines. The apex of the circular cone 72 faces distally to facilitate the insertion of a shaft of a medical instrument in the sealing device through a centering effect.

In the illustrated example, the outer edge 52 of the sealing lip 50 is arranged between two planes defined by the proximal and distal surface of the support portion 40. Therefore, both the proximal and the distal surface of the transition region 60 each have a conical shape, similar to the sealing device shown with reference to FIG. 6.

The proximal surface of the sealing lip 50 is flush with the proximal surface of the transition region 60. The proximal surfaces of the sealing lip 50 and of the transition region 60 form the same angle with the longitudinal axis 28 of a shaft inserted in the designated center position and orientation in the sealing device 30.

Figure 9:
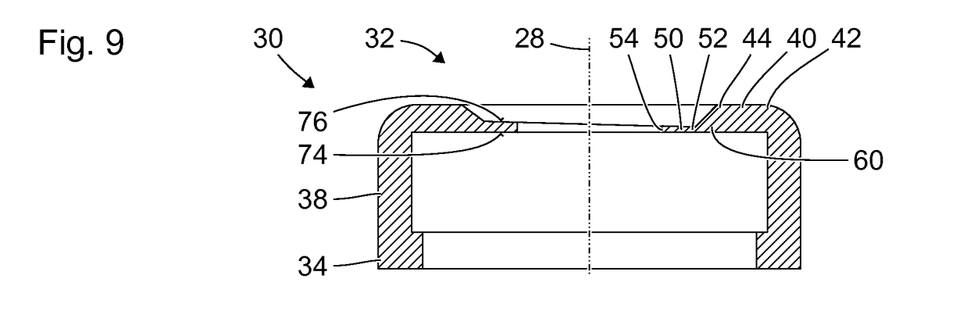
FIG. 9 is a schematic representation of a cross-section of a further sealing device.

FIG. 9 shows a schematic representation of a section through a further sealing device 30, which in some features, properties and functions is similar to the sealing devices illustrated with reference to FIGS. 1 to 8. The type of display is similar to that of FIGS. 1 to 4 and particularly of FIGS. 5 to 8. Below, in particular features, properties and functions are shown in which the sealing device shown in FIG. 9 differs from the sealing devices illustrated with reference to FIGS. 1 to 8.

The sealing device 30 shown in FIG. 9 differs from the sealing devices illustrated with reference to FIGS. 1 to 8 in particular in that the sealing lip 50 does not have a constant thickness. Rather, the thickness of the sealing lip 50 varies in the direction of its circumference. In the illustrated example, the proximal and the distal surface of the sealing lip 50 are each planar, wherein the surface normals form an angle of about 1.5 degrees. Since the sectional plane shown in FIG. 9 is selected such that the surface normals of the two surfaces of the sealing lip 50 lie in the sectional plane, the minimum thickness and (left) the maximum thickness of the sealing lip 50 are visible in FIG. 9 (right).

Figure 10:
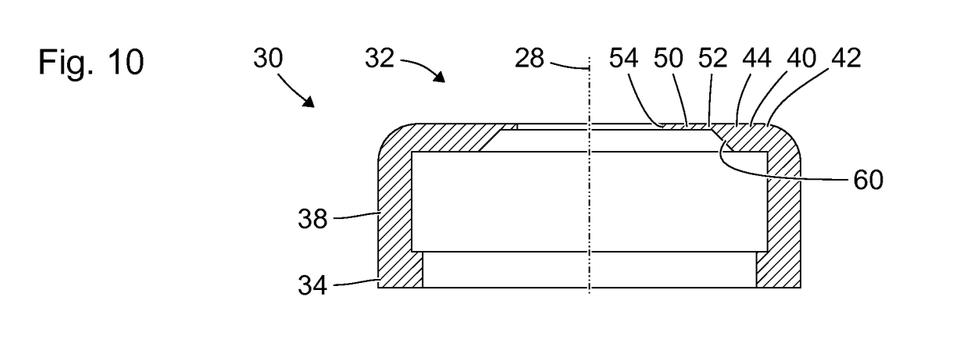
FIG. 10 is a schematic representation of a cross-section of a further sealing device.

FIG. 10 shows a schematic representation of a section through a further sealing device 30, which is similar in some features, properties, and functions to the sealing devices illustrated with reference to FIGS. 1 to 9. The type of display is similar to that of FIGS. 1 to 4 and particularly of FIGS. 5 to 9. Below, in particular features, properties and functions are shown in which the sealing device shown in FIG. 10 differs from the sealing devices illustrated with reference to FIGS. 1 to 9.

The sealing device 30 shown in FIG. 10 differs from the sealing devices illustrated with reference to FIGS. 1 to 9 in particular in that the sealing lip 50 has a varying width along its circumference. For example, both the outer rim 52 and the inner edge 54 of the sealing lip 50 are circular, wherein the centers of both edges 52, 54 are spaced apart from each other. In the illustrated example, the center of the inner edge 54 of the sealing lip 50 is located on the longitudinal axis 28 of a shaft inserted in the designated center position and orientation in the sealing device 30.

Figure 11:
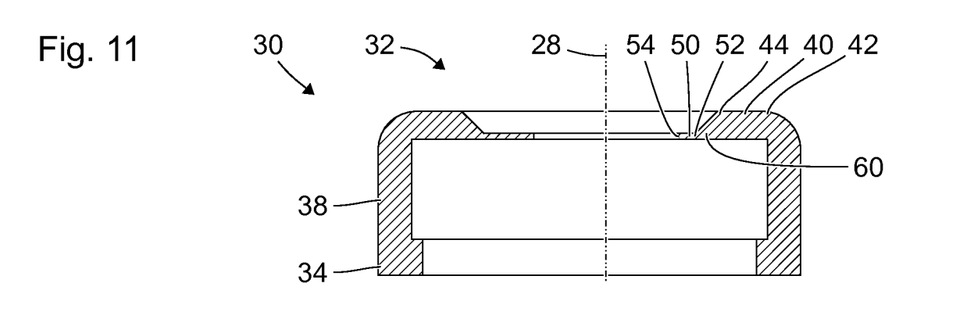
FIG. 11 is a schematic representation of a cross-section of a further sealing device.

FIG. 11 shows a schematic representation of a section through a further sealing device 30, which in some features and functions is similar to the sealing device shown with reference to FIGS. 1 to 10. The type of display is similar to that of FIGS. 1 to 4 and particularly of FIGS. 5 to 10. Below, features, properties and functions are shown in which the sealing device illustrated in FIG. 11 differs from the sealing devices illustrated with reference to FIGS. 1 to 10.

The sealing device 30 shown in FIG. 11 differs from the sealing device illustrated with reference to FIG. 10 especially in that the sealing lip 50 is not arranged flush with the proximal surface of the support portion 40 as in the sealing devices illustrated with reference to FIGS. 5 and 10, but instead arranged flush with the distal surface of the support portion 40, similar to the sealing devices shown in FIGS. 1 to 4, 7 and 9. Further, the sealing device 30 shown in FIG. 11 differs from the one illustrated with reference to FIG. 10 in that the inner edge 54 of the sealing lip 50 is positioned eccentrically. For example, the inner edge 44 of the support portion 40, the outer edge 52 and the inner edge 54 of the sealing lip 50 are each circular, wherein the center points of the inner edge 44 of the support portion 40 and of the outer edge 52 of the sealing lip 50 are located on an axis of symmetry of the sealing device 30 not shown in FIG. 11. The center of the inner edge 54 of the sealing lip 50 and thus the longitudinal axis 28 of a shaft inserted in the designated center position and orientation in the sealing device 30 is spaced from the axis of symmetry of the sealing device 30.

Figure 12:
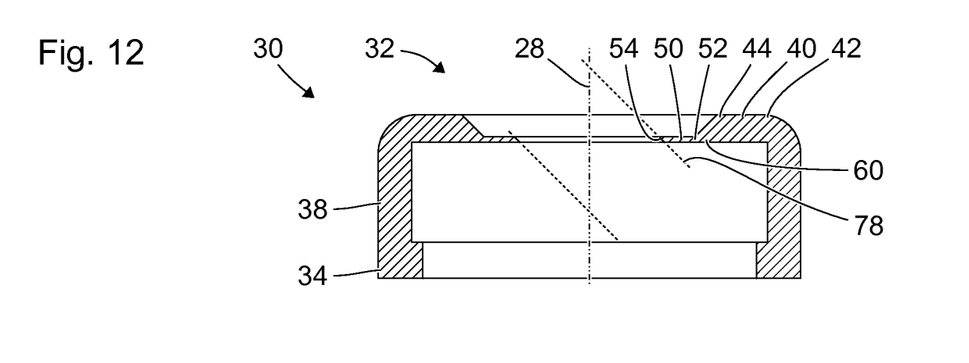
FIG. 12 is a schematic representation of a cross-section of a further sealing device.

FIG. 12 shows a schematic representation of a section through a further sealing device 30 which is similar in some features, properties and functions to the sealing devices illustrated with reference to FIGS. 1 to 11. The type of display is similar to that of FIGS. 1 to 4 and particularly of FIGS. 5 to 11. Below, in particular features, properties and functions are shown in which the sealing device shown in FIG. 12 differs from the sealing devices illustrated with reference to FIGS. 1 to 11.

The sealing device 30 shown in FIG. 12 differs from the sealing devices illustrated with reference to FIGS. 1 to 11 in particular in the design of the inner edge 54 of the sealing lip 50. In the embodiments illustrated with reference to FIGS. 1 to 11, the inner edge 54 is in each case indicated in the shape of a narrow annular cut-out of a lateral surface of a circular cylinder, wherein the axis of symmetry of the circular cylinder is coincident with the longitudinal axis 28 of a shaft inserted into the designated center position and orientation in the sealing device 30. In the sealing device 30 shown in FIG. 12, the inner edge 54 of the sealing lip 50 has the shape of a narrow annular cut-out from a lateral surface of a cylinder 78 indicated in FIG. 12 by dashed lines, of which the axis of symmetry (i.e. the direction of translation invariance) is not parallel to the longitudinal axis 28 of a shaft of a medical instrument inserted in the designated center position and orientation in the sealing device 30. Rather, the symmetry axis of the cylinder 78 and the longitudinal axis 28 form an angle, which is for example in the range from 15 degrees to 45 degrees and in particular is approximately 30 degrees.

Figure 13:
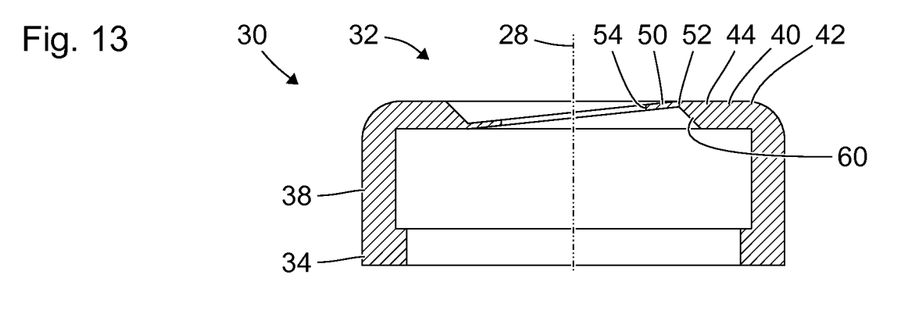
FIG. 13 is a schematic representation of a cross-section of a further sealing device.

FIG. 13 shows a schematic representation of a section through a further sealing device 30, which in some features, properties and functions is similar to the sealing device shown with reference to FIGS. 1 to 12. The type of display is similar to that of FIGS. 1 to 4 and particularly of FIGS. 5 to 12. Below, in particular features, properties and functions are shown in which the sealing device shown in FIG. 13 differs from the sealing devices illustrated with reference to FIGS. 1 to 12.

The sealing device 30 shown in FIG. 13 differs from the sealing devices illustrated with reference to FIGS. 1 to 12 in particular in that the sealing lip 50 is not parallel to a plane orthogonal to the longitudinal axis 28 of a shaft inserted in the designated center position and orientation in the sealing device 30. Instead, the sealing lip 50 is arranged tilted. In the illustrated example, the outer edge 52 of the sealing lip 50 is flush on one side with the distal surface of the support portion 60 (in FIG. 13: left), and flush on the opposite side with the proximal surface of the support portion 60 (in FIG. 13: right).

Figure 14:
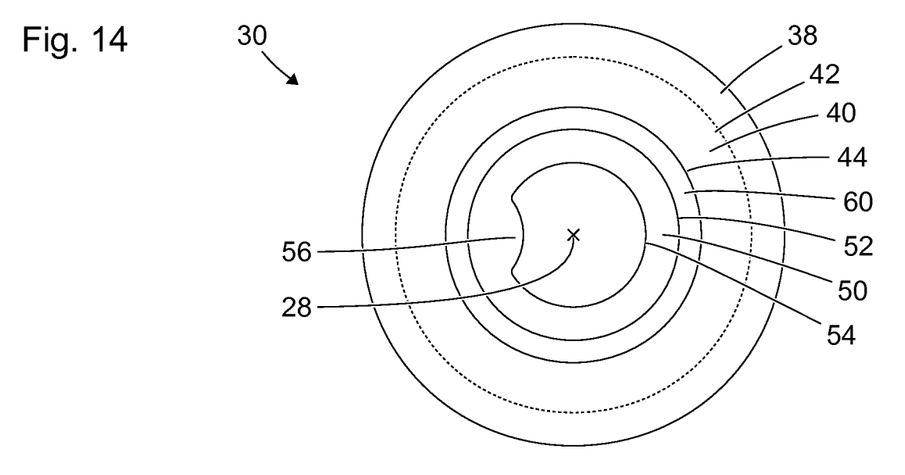
FIG. 14 is a schematic plan view of a further sealing device.

FIG. 14 shows a schematic plan view of a sealing device 30, which is similar in some features, properties and functions to the sealing devices shown with reference to FIGS. 1 to 13. The drawing plane of FIG. 14 is orthogonal to the section planes of FIGS. 1 to 13 and to the longitudinal axis 28 of a shaft inserted in the designated center position and orientation in the sealing device 30. The sealing device 30 is shown in a view from the proximal end so that the proximal side 32 (see FIGS. 1 to 13) is visible. The contour of the inner surface of the cylindrical wall 38 of the sealing device 30 is indicated by a broken line.

In the example shown, the cylindrical wall 38 of the sealing device 30 has the shape of a cut-out of a lateral surface of a circular cylinder. Therefore, the contours of its cross-sections are each circular. The inner edge 44 of the support portion 40 and the outer edge 52 of the sealing lip 50 are also both circular, wherein all the circle center points lie on the longitudinal axis 28 of a shaft inserted in the designated center position and orientation in the sealing device 30. Deviating from this mostly rotational symmetry of the sealing device, a tongue 56 on the sealing lip 50 is provided which projects into the shaft opening that is enclosed by the sealing lip 50. Therefore, the inner edge 54 of the sealing lip 50 has a shape which deviates in the region of the tongue 56 from a pure circular shape.

Figure 15:
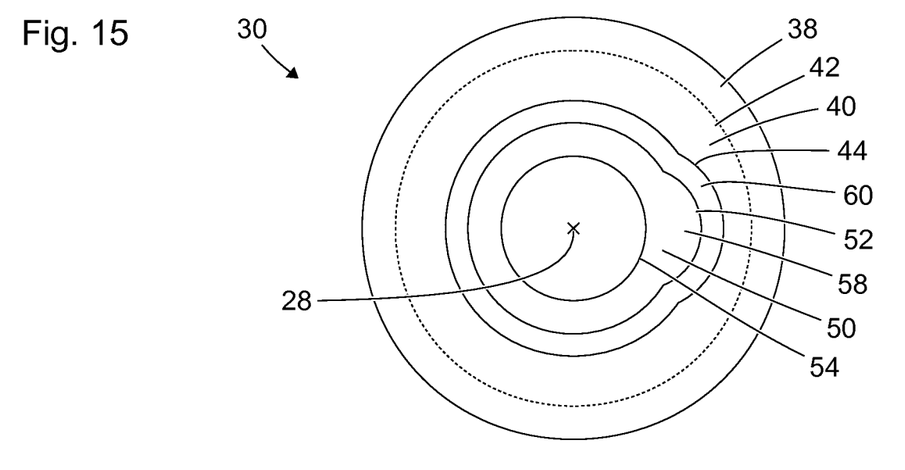
FIG. 15 is a schematic plan view of a further sealing device.

FIG. 15 shows a schematic representation of a plan view of a further sealing device 30, which in some features, properties and functions is similar to the sealing devices illustrated with reference to FIGS. 1 to 14. The type of display corresponds to that of FIG. 14. Below, in particular characteristics, features and functions are described in which the sealing device 30 shown in FIG. 15 differs from the sealing devices illustrated with reference to FIGS. 1 to 14.

In the sealing device 30 shown in FIG. 15, the sealing lip 50 has a bay-like widened portion 58. The outer edge 52 of the sealing lip 50 and the inner edge 44 of the support portion 40 have a shape that deviates from the form of a circle at or adjacent to the bay-like widened portion 58 of the sealing lip. The inner edge 54 of the sealing lip 50 is circular.

Figure 16:
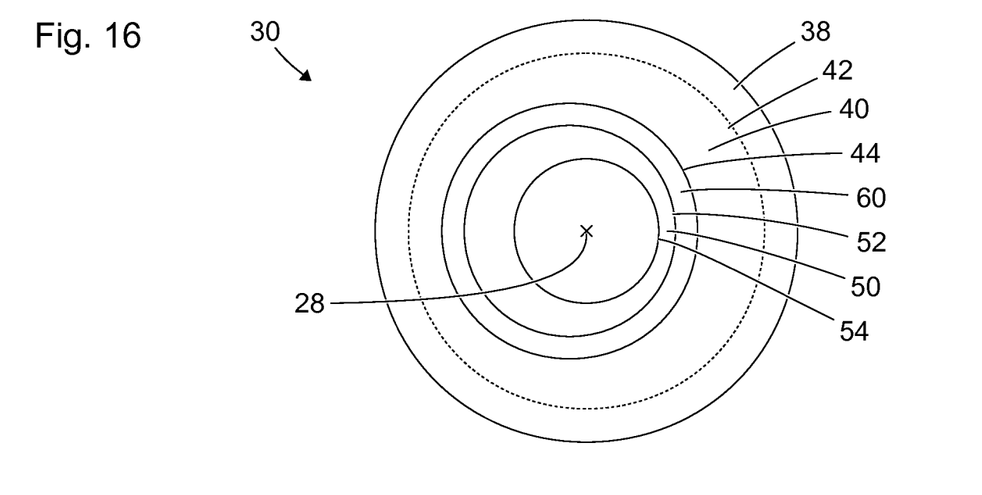
FIG. 16 is a schematic plan view of a further sealing device.

FIG. 16 shows a schematic representation of a plan view of a further sealing device 30, which is similar in some features, properties and functions to the sealing device illustrated with reference to FIGS. 1 to 15. The type of display corresponds to that of FIGS. 14 and 15. Below, features, properties and functions are described in which the sealing device 30 shown in FIG. 16 differs from the sealing devices illustrated with reference to FIGS. 1 to 15.

In the sealing device 30 shown in FIG. 16, the inner edge 44 of the support portion 40, the outer edge 52 and the inner edge 54 of the sealing lip 50 each have the shape of a circle, wherein the center points of the inner edge 44 of the support portion 40 and of the outer edge 52 of the sealing lip 50 are displaced with respect to the symmetry axis of other properties of the sealing device 30, in particular with respect to the center of the inner edge 54 of the sealing lip 50. Therefore, the sealing lip 50 has a varying width along its circumference, similar to the sealing devices illustrated with reference to FIGS. 10, 11, 14 and 15.

Figure 17:
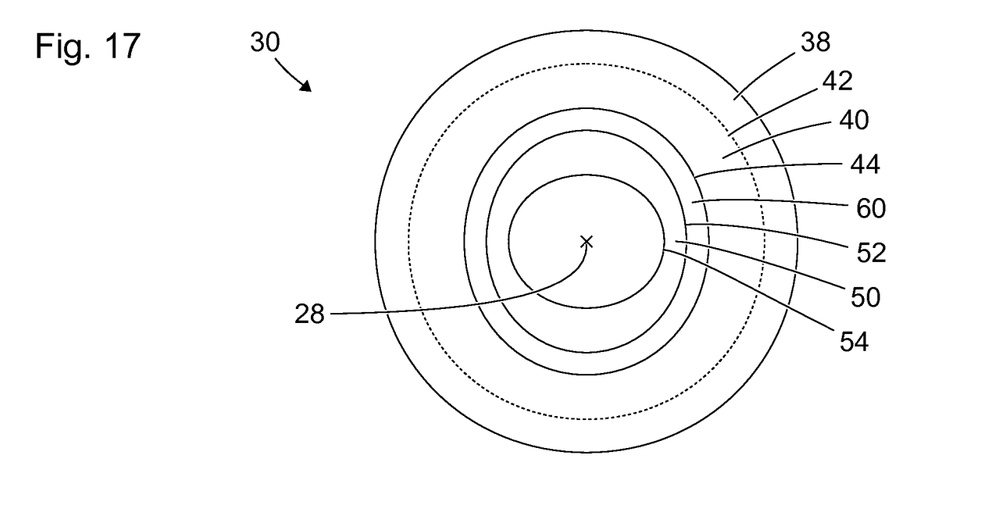
FIG. 17 is a schematic plan view of a further sealing device.

FIG. 17 shows a schematic representation of a plan view of a further sealing device 30, which is similar in some features, properties and functions to the sealing devices illustrated with reference to FIGS. 1 to 16. The type of display corresponds to that of FIGS. 14 through 16. Below, features, properties and functions are described in which the sealing device 30 shown in FIG. 17 differs from the sealing devices illustrated with reference to FIGS. 1 to 16.

In the sealing device 30 shown in FIG. 17, the inner edge 44 of the support portion 40, the outer edge 52 and the inner edge 54 of the sealing lip 50 each have the shape of an ellipse, wherein the area center points of the ellipses lie on the axis of symmetry of other features of the sealing device 30 and of the longitudinal axis 28 of a shaft inserted in the designated center position and orientation in the sealing device 30. In the illustrated example, the large major axes of the elliptical inner edge 44 of the support portion 40 and of the elliptical outer edge 52 of the sealing lip 50 are parallel to the small major axis of the elliptical inner edge 54 of the sealing lip 50, and the small major axes of the elliptical inner edge 44 of the support portion 40 and of the elliptical outer edge 52 of the sealing lip 50 are parallel to the major axis of the elliptical inner edge 54 of the sealing lip 50. Therefore, the sealing lip 50 has a continuously varying width along its circumference.

Figure 18:
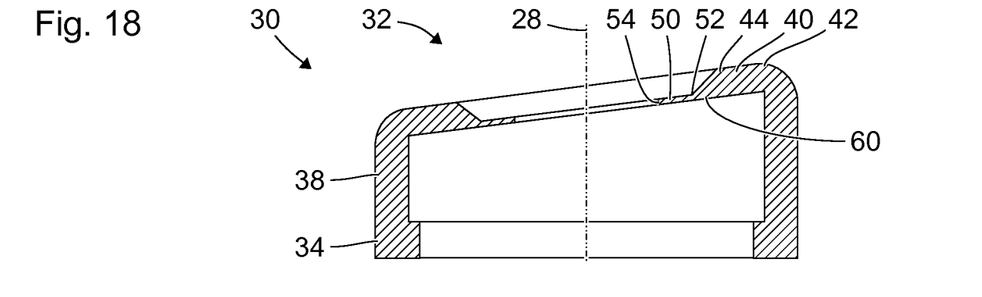
FIG. 18 is a schematic representation of a cross-section of a further sealing device.

FIG. 18 shows a schematic representation of a section through a further sealing device 30, which is similar in some features, properties, and functions to the sealing devices illustrated in FIGS. 1 to 17. The type of display is similar to that of FIGS. 1 to 4 and particularly of FIGS. 5 to 13. Below, in particular features, properties and functions are shown in which the sealing device shown in FIG. 18 differs from the sealing devices illustrated with reference to FIGS. 1 to 17.

The sealing device 30 shown in FIG. 18 differs from the sealing devices illustrated with reference to FIGS. 1 to 12 in particular in that the sealing lip 50 is not parallel to a plane orthogonal to the longitudinal axis 28 of a shaft inserted in the designated center position and orientation in the sealing device 30. Therein, the sealing device shown in FIG. 18 is similar to the sealing device 30 illustrated with reference to FIG. 13.

In contrast to the sealing devices illustrated with reference to FIGS. 1 to 12 and in contrast to the sealing device illustrated with reference to FIG. 13, however, in the sealing device 30 shown in FIG. 18, the support portion 40 is not disposed in a plane orthogonal to the longitudinal axis 28 of a shaft inserted in the designated center position and orientation in the sealing device 30. Rather, both the support portion 40 and the sealing lip 50 are arranged parallel or substantially parallel to a plane that is tilted with respect to the longitudinal axis 28. In the illustrated example, the normal of a plane to which the supporting portion 40 and the sealing lip 50 are parallel or substantially parallel, forms an angle in the range of 5 degrees to 10 degrees with the longitudinal axis 28 of a shaft inserted in the designated center position and orientation in the sealing device 30. However, the angle may alternatively be less than 5 degrees or greater than 10 degrees.

In the sealing devices illustrated with reference to FIGS. 1 to 18, in particular in the sealing devices illustrated with reference to FIGS. 1 to 13 and 18, the support portions are formed in each case as annular cut-outs of planar plates. Thus, the support portions each have a planar or substantially planar proximal surface portion and a flat and substantially planar distal surface portion which are parallel to each other. Deviating from this, the entire support portions or the proximal surface areas and/or the distal surface portions of the support portions can each have the shape of ring-shaped cutouts of curved surfaces, for example, of spherical surfaces or surfaces of other ellipsoids of revolution.

In FIGS. 1 to 18, in particular in FIGS. 1 to 13 and 18, the cross sections are each indicated as homogeneous. Thus, the sealing devices 30 shown each formed a single material which forms both the supporting portion 40 and the sealing lip 50, and in particular the cylindrical wall 38 and the inwardly projecting collar 36 (as the fastening area). Deviating from this, each of the illustrated sealing devices may have several different materials, wherein areas of different materials are in particular integrally and/or positively connected with each other. For example, the sealing lip may be formed from a comparatively soft material, and the support portion or a part of the support portion or the cylindrical wall 38 may be formed from a comparatively hard material.

In the sealing devices 30 illustrated with reference to FIGS. 9 to 18, the sealing lips 50 are each non-rotationally symmetrical to the longitudinal axis 28 of a shaft inserted in the designated center position and orientation in the sealing device 30. The deformation of the sealing lip 50 by a shaft inserted into the sealing device 30—as shown with reference to FIG. 2—therefore causes an elastic deformation and a concomitant mechanical tension within the sealing lip 50 as well as a contact pressure of the sealing lip 50 on the outer surface of the shaft, which are not rotationally symmetrical but vary along the circumference of the sealing lip 50. This may encourage a gradual instead of a sudden and simultaneous folding or turning over of the sealing lip 50 with a reversal of the direction of movement of a shaft in the sealing device 30. A gradual folding of the sealing lip 50 originates—among other things dependent on the friction between the sealing lip 50 and the outer surface of the shaft—for example, from the point at which the sealing lip 50 has the greatest width or the smallest thickness, and spreads from this location proceeding along the circumference of the sealing lip until the sealing lip 50 is completely folded. The gradual folding of the sealing lip 50 is less noticeable and is perceived as less bothersome by the medical staff.

In all sealing devices shown with reference to FIGS. 1 to 18, the entire surface or at least part or multiple parts of the surface of the sealing lip 40 may be designed or coated to reduce friction. For example, the entire surface or part of the surface of the sealing lip 40 may be coated with poly (p-xylylene), which is also marketed under the trade name Parylene. Friction-reducing coating may reduce static and/or sliding friction between the sealing device 30 and a medical instrument inserted into the sealing device 30.

Features of the sealing devices illustrated with reference to FIGS. 1 to 18 can partially be combined with one another. For example, in the sealing devices illustrated with reference to FIGS. 9 to 18, the sealing lips and the transition regions may be arranged and designed similar to the sealing devices shown with reference to FIGS. 5 to 8. Further, an asymmetrical design of the sealing lip 50 similarly as shown with reference to FIGS. 9 to 18 may exist even if the sealing lip 50 and the support portion 40 are not clearly distinguishable from each other, but for example, seamlessly merge into each other with a shared wedge-shaped cross-section.

The invention being thus described, it will be obvious that the same may be varied in many ways. Such variations are not to be regarded as a departure from the spirit and scope of the invention, and all such modifications as would be obvious to one skilled in the art are to be included within the scope of the following claims.

What is claimed is:

1. A sealing device for sealing a lead-through for a shaft of a medical instrument, comprising:
a fastening area for fastening the sealing device on a tube or other medical device;
an annular support portion, which is connected to the fastening area;
an annular sealing lip with an outermost distal edge, which is directly connected to an inner edge of the annular support portion, and an inner edge, which is provided as an opening through which the shaft of the medical instrument inserted in the sealing device extends, the inner edge of the annular sealing lip designed to fluid-tightly abut an outer surface of the shaft,
wherein the annular support portion is oriented perpendicular to a longitudinal axis of the shaft, and wherein the fastening area is connected to the annular support portion by a cylindrical wall, the cylindrical wall being oriented parallel to the longitudinal axis of the shaft,
wherein an outer edge of the annular support portion directly connects to an upper end of the cylindrical wall and a lower end of the cylindrical wall directly connects to the fastening area,
wherein the fastening area is an inwardly projecting collar that projects towards an axis of the opening of the annular sealing lip,
wherein the annular support portion, the annular sealing lip, the fastening area and the cylindrical wall are monolithic,
wherein the annular support portion extends continuously around a periphery of the upper end of the cylindrical wall,
wherein a thickness of an entirety of the annular support portion is larger than a thickness of the annular sealing lip, and
wherein, in a mechanically tension-free state of the annular sealing lip, a bottom surface of the annular sealing lip extends in a same plane as a bottom surface of the annular support portion, the bottom surface of the annular support portion being a single surface that extends continuously on the same plane and terminates at an inner surface of the upper end of the cylindrical wall, wherein the bottom surface of the annular sealing lip and the bottom surface of the annular support portion face the inwardly projecting collar.

2. The sealing device according to claim 1, wherein the annular sealing lip is non-rotationally symmetrical to the longitudinal axis of the shaft inserted in a designated center position and orientation in the sealing device.

3. The sealing device according to claim 1, wherein, in a mechanically tension-free state, the annular sealing lip, from the inner edge to the outermost distal edge, is formed of flat, planar surfaces.

4. The sealing device according to claim 1, wherein at least either: the difference of the circumference of the inner edge of the annular support portion and the periphery of the shaft of the medical instrument, for which the sealing device is provided and designed, is not larger than the difference of the circumference of the shaft and the circumference of the inner edge of the annular sealing lip in its stress-free state, or the difference of the average diameter of the inner edge of the annular support portion and the mean diameter of the shaft of the medical instrument, for which the sealing device is provided and designed, is not larger than the difference of the average diameter of the shaft and the mean diameter of the inner edge of the annular sealing lip.

5. A sealing device for sealing a lead-through for a shaft of a medical instrument, comprising:
a fastening area for fastening the sealing device on a tube or other medical device;
an annular support portion, which is connected to the fastening area; and
an annular sealing lip having an inner edge which is provided as an opening through which the shaft of the medical instrument inserted in the sealing device extends, the inner edge of the annular sealing lip designed to abut fluid-tightly at an outer surface of the shaft, and the annular sealing lip having an outer edge which is directly connected to an inner edge of the annular support portion,
wherein, in a mechanically tension-free state, the annular sealing lip is not rotationally symmetrical,
wherein, in the mechanically tension-free state, the annular sealing lip, from the inner edge to the outer edge, is formed of flat, planar surfaces,
wherein the annular support portion is oriented perpendicular to a longitudinal axis of the shaft, and wherein the fastening area is connected to the annular support portion by a cylindrical wall, the cylindrical wall being oriented parallel to the longitudinal axis of the shaft,
wherein an outer edge of the annular support portion directly connects to an upper end of the cylindrical wall and a lower end of the cylindrical wall directly connects to the fastening area,
wherein the fastening area is an inwardly projecting collar that projects towards an axis of the opening of the annular sealing lip,
wherein the annular support portion, the annular sealing lip, the fastening area and the cylindrical wall are monolithic, and
wherein an entire upper surface of the annular sealing lip extends on a same first plane and an entire bottom surface of the annular sealing lip extends on a same second plane, and wherein the bottom surface of the annular sealing lip faces the inwardly projecting collar and the upper surface of the annular sealing lip opposes the bottom surface of the annular sealing lip.

6. The sealing device according to claim 5, wherein at least either the inner edge or the outer edge of the annular sealing lip is non-circular.

7. The sealing device according to claim 5, wherein, in the mechanically tension-free state, the centroid of the area limited by the inner edge of the annular sealing lip is spaced apart from the centroid limited by the outer edge of the annular sealing lip.

8. The sealing device according to claim 5, wherein the annular sealing lip in the mechanically tension-free state has a varying thickness in the direction of its circumference.

9. The sealing device according to claim 8, wherein surface normals of two surfaces of the annular sealing lip facing away from each other at opposing locations on the surfaces in the mechanically tension-free state of the annular sealing lip are not parallel, and wherein a first one of the two surfaces faces toward an interior of the sealing device and a second one of the two surfaces faces toward an exterior of the sealing device.

10. The sealing device according to claim 5, wherein the inner edge of the annular sealing lip has the shape of a section of an outer circular surface of a cylinder, of which the symmetry axis is not parallel to the average surface normal of two surfaces of the annular sealing lip facing away from each other.

11. The sealing device according to claim 5, wherein the average surface normal of the annular sealing lip is not parallel to the longitudinal axis of the shaft inserted in the designated center position and orientation in the sealing device.

12. The sealing device according to claim 5, wherein the periphery of the inner edge of the annular sealing lip is at least six tenths and at most nine tenths of the periphery of the shaft of the medical instrument, for which the sealing device is provided and designed.

13. The sealing device according to claim 5, wherein the average thickness of the annular sealing lip amounts to at most a fifth of the average thickness of the annular support portion.

14. The sealing device according to claim 5, wherein the annular sealing lip in the mechanically tension-free state has a continuously varying thickness in the direction of its circumference.

15. The sealing device according to claim 5, wherein the sealing device is fastened to the tube.

16. The sealing device according to claim 5, wherein, in a mechanically tension-free state, a portion of the inner edge of the annular sealing lip has a tongue that protrudes inward toward a center of the opening, such that the tongue projects farther towards the center of the opening than a remainder of the inner edge of the annular sealing lip.

17. A sealing device for sealing a lead-through for a shaft of a medical instrument, comprising:
a fastening area for fastening the sealing device on a tube or other medical device;
an annular support portion, which is connected to the fastening area;
an annular sealing lip with an outermost distal edge, which is directly connected to an inner edge of the annular support portion, and an inner edge, which is provided as an opening through which the shaft of the medical instrument inserted in the sealing device extends, the inner edge of the annular sealing lip designed to fluid-tightly abut an outer surface of the shaft,
wherein, in a mechanically tension-free state, the annular sealing lip, from the inner edge to the outer edge, is formed of flat, planar surfaces and wherein, in the mechanically tension-free state, a portion of the inner edge of the annular sealing lip has a tongue that protrudes inward toward a center of the opening, such that the tongue projects farther towards the center of the opening than a remainder of the inner edge of the annular sealing lip,
wherein an entire upper surface of the annular sealing lip extends on a same first plane and an entire bottom surface of the annular sealing lip extends on a same second plane, and wherein the bottom surface of the annular sealing lip faces an interior of the sealing device and the upper surface of the annular sealing lip faces an exterior of the sealing device, and wherein the bottom surface of the annular sealing lip extends in a same plane as a bottom surface of the annular support portion.

18. The sealing device according to claim 17, wherein at least either: the difference of the circumference of the inner edge of the annular support portion and the periphery of the shaft of the medical instrument, for which the sealing device is provided and designed, is not larger than the difference of the circumference of the shaft and the circumference of the inner edge of the annular sealing lip in its stress-free state, or the difference of the average diameter of the inner edge of the annular support portion and the mean diameter of the shaft of the medical instrument, for which the sealing device is provided and designed, is not larger than the difference of the average diameter of the shaft and the mean diameter of the inner edge of the annular sealing lip.

* * * * *